United States Patent
Lo et al.

(10) Patent No.: US 10,736,567 B2
(45) Date of Patent: Aug. 11, 2020

(54) CARPET TYPE BODY FAT MONITOR STRUCTURE

(71) Applicant: CAL-COMP BIG DATA, INC., New Taipei (TW)

(72) Inventors: Teng-Nan Lo, New Taipei (TW); Te-Kai Ku, New Taipei (TW); Nai-Chiang Pai, New Taipei (TW); Chun-An Hsu, New Taipei (TW); Shyh-Yong Shen, New Taipei (TW)

(73) Assignee: CAL-COMP BIG DATA, INC., New Taipei (TW)

( * ) Notice: Subject to any disclaimer, the term of this patent is extended or adjusted under 35 U.S.C. 154(b) by 282 days.

(21) Appl. No.: 15/459,929

(22) Filed: Mar. 15, 2017

(65) Prior Publication Data
US 2018/0103900 A1  Apr. 19, 2018

(30) Foreign Application Priority Data
Oct. 14, 2016 (TW) .............................. 105133193 A

(51) Int. Cl.
*A61B 5/00* (2006.01)
*A61B 5/053* (2006.01)
*A61B 5/103* (2006.01)

(52) U.S. Cl.
CPC .......... *A61B 5/4872* (2013.01); *A61B 5/0537* (2013.01); *A61B 5/1036* (2013.01); *A61B 5/6892* (2013.01)

(58) Field of Classification Search
CPC ... A61B 5/4872; A61B 5/1036; A61B 5/6892; A61B 5/0537
See application file for complete search history.

(56) References Cited

U.S. PATENT DOCUMENTS 5,695,859 A * 12/1997 Burgess ................. H01H 1/029
                                                                 200/85 R
6,721,980 B1 * 4/2004 Price ..................... A61B 5/0205
                                                                 5/710
(Continued)

FOREIGN PATENT DOCUMENTS

CN    204388895 U    6/2015
CN    104783793 A    7/2015
(Continued)

OTHER PUBLICATIONS

EPO Machine Translation of JP 2015213607. Generated on Feb. 13, 2019. (Year: 2019).*
(Continued)

*Primary Examiner* — Matthew Kremer
*Assistant Examiner* — Samuel C Kim
(74) *Attorney, Agent, or Firm* — Chun-Ming Shih; HDLS IPR Services

(57) ABSTRACT

A body fat monitor structure includes a foot pad and a body fat monitor disposed in the body fat monitor. The foot pad includes a base layer and a cloth layer laminated on the base layer. The base layer has a hollow area, and the body fat monitor is accommodated in the hollow area. The body fat monitor includes housing and a set of measurement components disposed in the housing. The set of measurement components at least has an electrical contact exposed from the housing, the cloth layer has a sensor portion disposed corresponding to the electrical contact, and the sensor portion is configured by conductive yarn knitted on the cloth layer and exposed between an upper and a lower surfaces of the cloth layer.

13 Claims, 4 Drawing Sheets

(56) References Cited

U.S. PATENT DOCUMENTS

| | | | | |
|---|---|---|---|---|
| 2008/0200793 | A1* | 8/2008 | Furue | A61B 5/0537 600/393 |
| 2013/0137943 | A1* | 5/2013 | Pinto Rodrigues | A61B 5/01 600/301 |
| 2013/0201150 | A1* | 8/2013 | Suzuki | G06F 3/03547 345/174 |
| 2013/0263791 | A1* | 10/2013 | Crisanaz | A01K 1/0107 119/171 |
| 2015/0342498 | A1* | 12/2015 | Kumagai | A61B 5/0537 600/547 |
| 2015/0359488 | A1* | 12/2015 | Hsu | A61B 5/6892 600/595 |
| 2017/0035303 | A1* | 2/2017 | Sullivan | A61B 5/6892 |
| 2017/0188963 | A1* | 7/2017 | Banet | A61B 5/6892 |

FOREIGN PATENT DOCUMENTS

| | | | |
|---|---|---|---|
| JP | 2008279181 | A | 11/2008 |
| JP | 2015213607 | A | 12/2015 |

OTHER PUBLICATIONS

"Reed". Merriam-Webster.com. 2019. Retrieved on Feb. 19, 2019, from https://www.merriam-webster.com/dictionary/reed. (Year: 2019).*

"Embedded". Merriam-Webster.com. 2019. Retrieved on Jul. 23, 2019, from www.merriam-webster.com/dictionary/embedded (Year: 2019).*

Search Report dated Nov. 20, 2017 of the corresponding JP patent Publication No. 2015213607.

Office Action dated Jul. 24, 2018 of the corresponding Japan patent applicaiton.

Office Action dated Jan. 18, 2017 of the corresponding Taiwan patent applicaiton.

* cited by examiner

CARPET TYPE BODY FAT MONITOR STRUCTURE

BACKGROUND OF THE INVENTION

Field of the Invention

The present invention generally relates to a body fat monitor and, more particular to, a carpet type body fat monitor structure.

Description of Prior Art

With the social progress, the quality of life of modern people has improved. Especially, the intake of nutrients from diets has become rich so that an overweight might be occurred that will cause other diseases. Therefore, weight and body fat have become indicators for modern people to pay attention to health.

Presently, a body fat monitor on market can measure body weight and body fat at the same time, wherein the measurement of body fat is measured by, a sensor sheet for example, a micro current passing through a human body for sensing received signals as to determine the body fat percentage. Thus a sensor sheet made of metal material must be provided on the body fat monitor as a conductive site for contacting with the human body. Meanwhile, by contacting the feet (ankle) of human body with the conductive site, the body fat monitor can monitor the changing of the signal of the human body to calculate the body fat of users.

However, when the weather is cold, especially in winter, we human often feel cold and uncomfortable when feet stamp directly on the sensing sheet made of metal material. As a result, the frequency of using the body fat monitor by users will be easily reduced. Eventually, users might neglect their weight and body fat because users cannot keep using the body fat monitor to monitor those factors influencing their health condition. Then the health of the users may be ignored.

In view of the above drawbacks, the Inventor proposes the present invention based on his expert knowledge and elaborate researches in order to solve the problems of prior art.

SUMMARY OF THE INVENTION

Accordingly, an object of the present invention is to provide a carpet type body fat monitor structure, in which the conductive wool is provided as a barrier for avoiding cold temperature transmitted to feet of human through the metal-made electrical contact on one hand, and the effect of conduction between the body and body fat monitor can be maintained on the other hand; thereby, discomfort of coldness will not be a reason that decrease the willing of using the body fat monitor for users.

Accordingly, another object of the present invention is to provide a carpet type body fat monitor structure, in which the body fat monitor structure disposed of the wool looks like a carpet, thus aesthetics of interior decoration can be improved when it is disposed in the room.

In order to achieve the object mentioned above, the present invention provides a carpet type body fat monitor structure including a foot pad and a body fat monitor disposed in the foot pad. The foot pad includes a base layer and a cloth layer laminated on the base layer. The base layer has a hollow area, and the body fat monitor accommodated in the hollow area. The body fat monitor includes housing and a set of measurement components disposed in the housing. The set of measurement components at least has an electrical contact exposed from the housing, wherein the cloth layer has a sensor portion disposed corresponding to the electrical contact, and the sensor portion is configured by conductive yarn knitted on the cloth layer and exposed between an upper and a lower surfaces of the cloth layer. Therefore, the above objects can be achieved by the cloth layer of the foot pad and sensor portion knitted by the conductive yarn.

BRIEF DESCRIPTION OF DRAWING

The features of the invention believed to be novel are set forth with particularity in the appended claims. The invention itself, however, may be best understood by reference to the following detailed description of the invention, which describes a number of exemplary embodiments of the invention, taken in conjunction with the accompanying drawings, in which:

DETAILED DESCRIPTION OF THE PREFERRED EMBODIMENTS

In cooperation with attached drawings, the technical contents and detailed description of the invention are described thereinafter according to a number of preferable embodiments, being not used to limit its executing scope. Any equivalent variation and modification made according to appended claims is all covered by the claims claimed by the present invention.

Figure 1:
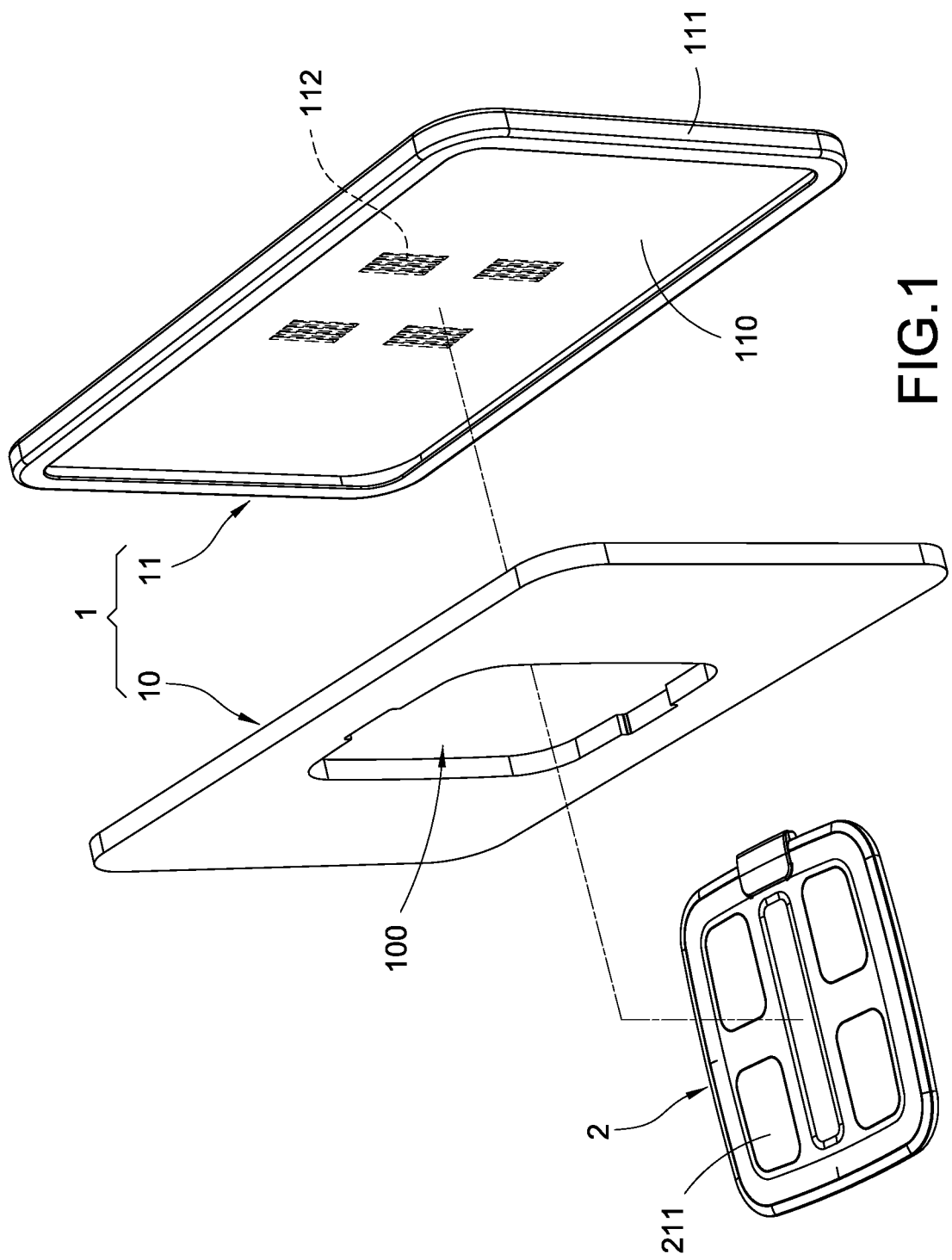
FIG. 1 is a perspective explosion schematic view of the present invention.
Figure 2:
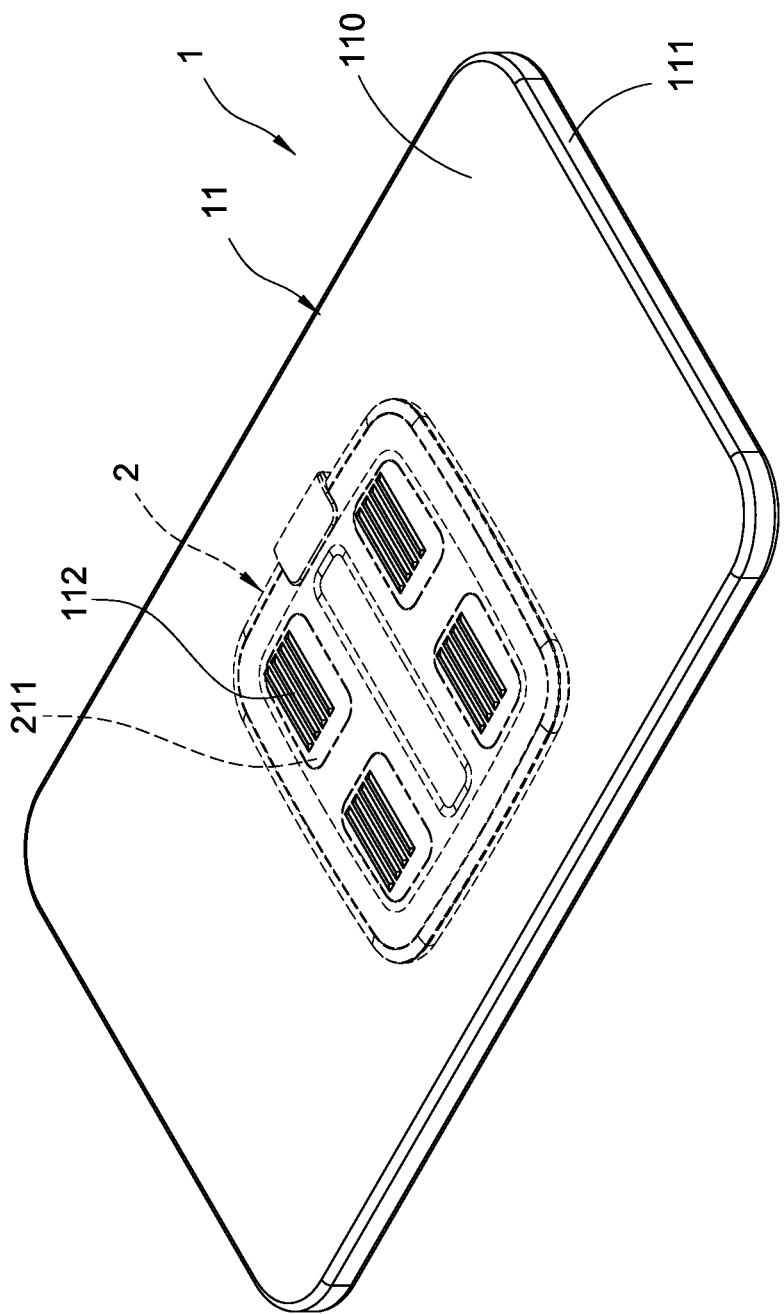
FIG. 2 is a perspective assembly schematic view of the present invention.
Figure 3:
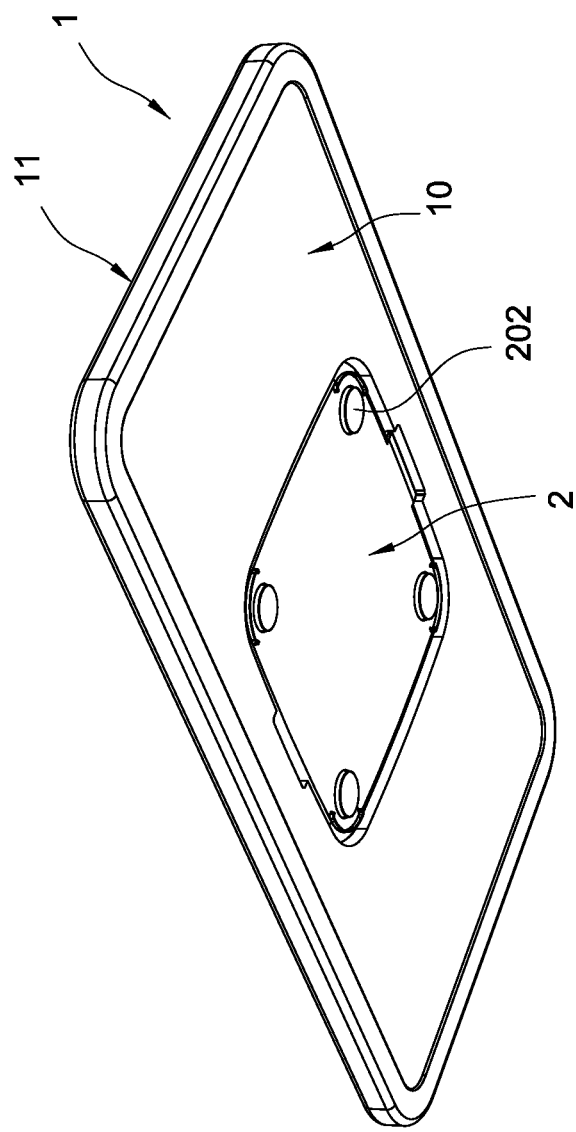
FIG. 3 is another view of a perspective assembly schematic view of the present invention.

Please refer to FIG. 1 to FIG. 3, they depict a perspective explosion schematic view, a perspective assembly schematic view and another view of a perspective assembly schematic view of the present invention. The present invention provides a carpet type body fat monitor structure that can be placed indoor, such as a bedroom or a bathroom, for users, and it can also be placed on a ground in front of a dressing table or a washstand for using conveniently. The carpet type body fat monitor structure includes a foot pad 1 and a body fat monitor 2 disposed in the foot pad 1.

The foot pad 1 includes a base layer 10 and a cloth layer 11. The base layer 10 can be made of rubber, hard sponge or foam material (e.g. EVA), and the base layer 10 has a hollow area 100 for the body fat monitor 2 accommodated therein. The cloth layer 11 can be constituted by a woven fabric and can be directly adhered to the base layer 10; or the cloth layer 11 can also comprise a barrier cloth 110 and a fold 111 surrounded at a periphery of the barrier cloth 110, wherein the barrier cloth 110 is a general blanket or a carpet, and an arbitrary pattern (not shown) can be woven on an upper surface of the barrier cloth 110 depending on appearance requirements for improving aesthetics. In addition, the fold 111 is provided as a local covering structure which is inwardly recessed from the periphery of the barrier cloth 110. The fold 111 and the barrier cloth 110 can be integrally knitted by the same textile material with certain flexibility for covering the base layer 10 at the periphery and let the base layer 10 laminated on a lower surface of the cloth layer 110. In other embodiments, the base layer 10 can also be made of a woven fabric or the like to woven integrally with the cloth layer 11.

Figure 4:
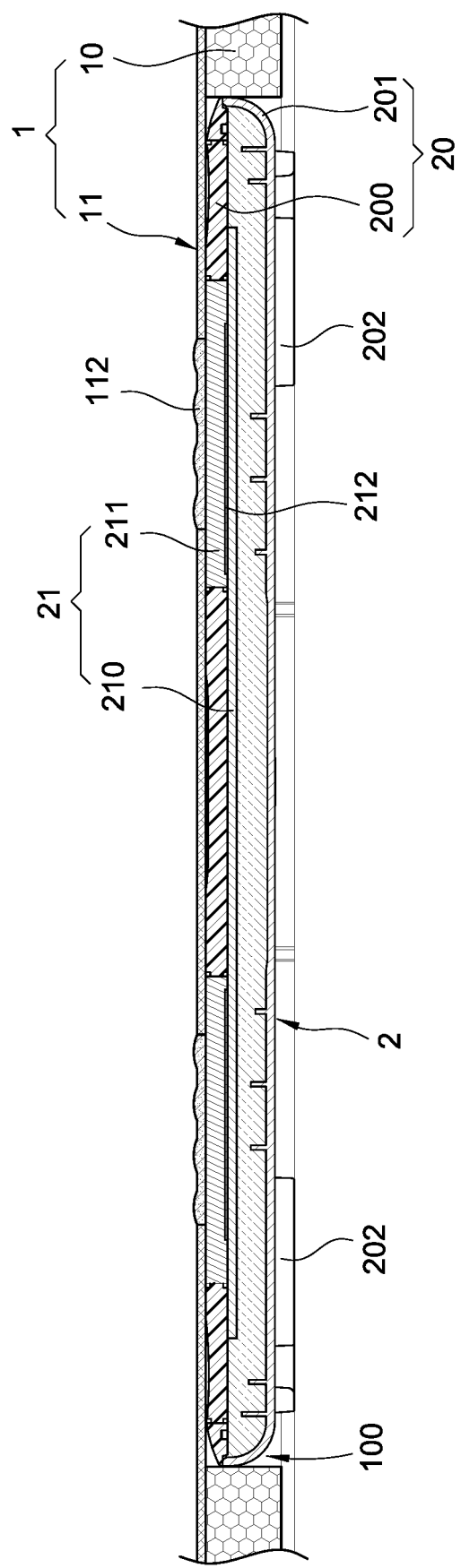
FIG. 4 is a partial cross sectional schematic view of the present invention.

As shown in FIG. 4, the body fat monitor 2 is accommodated in the hollow area 100 of the base layer 10 and includes a housing 20 and a set of measurement components 21 disposed in the housing 10, and the set of measurement components 21 at least has functions of measurement of body weight and body fat. With further, the housing 20 can be composed of an upper cover 200 and a base 201, and a plurality of foot pads 202 are arranged under the base 201 as to prevent from slipping. The set of measurement components 21 further comprises a control PCB 210 and an electrical contact 211 electrically connected with the control PCB 210. A conductive reed 212 is disposed between the electrical contact 211 and the control PCB 210. The electrical contact 211 is exposed from a surface of the upper cover 200 of the housing 20, and the electrical contact 211 is composed of a conductive metal or a conductive silicone. Thereby, when the human body presses against the electrical contact 211 by the weight, the electrical contact 211 will press the conductive reed 212 for sensing the weight of the human body, and then the electrical contact 211 will determine the body fat percentage by a micro current passing through a body for sensing the received signals through the conductive reed 212. However, this knowledge belongs to the conventional technology and is not the scope of the present invention that will not be descripted hereafter.

Please also refer to FIG. 1, FIG. 2 and FIG. 4, in the present invention, the cloth layer 11 has a sensor portion 112, which is electrically connected with the electrical contact 211 and disposed corresponding to the electrical contact 211. The sensor portion 112 is configured by conductive yarn knitted on the barrier cloth 110 of the cloth layer 11, and the conductive yarn is knitted between an upper and lower surfaces of the barrier sheet 110 back and forth for the sensing portion 112 can be exposed between the upper and lower surfaces of the cloth layer 11. As the conductive yarn is composed of a certain proportion of conductive fibers (such as stainless steel fibers) mixed with ordinary fiber, hence it have a property of conduction. When the human body stands on the foot pad 1 where the foot and the body fat meter 1 are separated from each other by the barrier cloth 110, a micro current still can be conducted through the sensing portion 112 configured by the conductive yarn and the electrical contact 211 of the body fat monitor 2. Therefore, the body fat structure 2 can calculate the body fat percentage for the human body.

It is worth of notice that after the body fat percentage is calculated by the body fat monitor 2 of the present invention, its value can be displayed through a display screen (not shown) of the body fat monitor 2 from a corresponding window provided on the barrier cloth 110. Moreover, the body fat monitor 2 can have a wireless transmitter (not shown) provided on the control circuit board 210, and a wireless receiver (not shown) is disposed in the mirror of the dressing table or washstand. In this way, the calculated value of the body fat percentage can be displayed on the mirror through wireless transmission.

Therefore, the carpet type body fat monitor structure of the present invention can be obtained by the above-mentioned deposition.

Furthermore, because of the cloth layer 11 of the foot pad 1 of the carpet type body fat monitor structure of the present invention, when the human body stamps on the body fat monitor 2, their feet will not directly contact the electrical contact 211 but contact the barrier cloth 110 made of cloth. As a result, there will be no discomfort of coldness but can feel the comfort of wool while the measurement function of the body fat monitor still can be maintained. Thereby, the chance that the user is unwilling to use the body fat monitor because of the discomfort of coldness can be decreased. Furthermore, the body fat monitor structure looks like a blanket or a carpet when it is arranged on the ground indoor through the cloth layer 11 covered thereon for improving aesthetics of interior decoration.

In summary, the present invention is a new creative product that can indeed achieve the intended purpose of use and solve the shortcomings of prior art. Besides, the present invention has novelty and progress that meets the requirements of a new patent application in accordance with the patent law. Therefore, the present is filed in accordance with the patent law for protecting the rights of the inventor.

Although the present invention has been described with reference to the preferred embodiment thereof, it will be understood that the invention is not limited to the details thereof. Various substitutions and improvements have been suggested in the foregoing description, and others will occur to those of ordinary skill in the art. Therefore, all such substitutions and improvements are intended to be embraced within the scope of the invention as defined in the appended claims.

What is claimed is:

1. A carpet type body fat monitor structure, including:
   a foot pad including a base layer and a cloth layer laminated on the base layer, and the base layer having a hollow area; and
   a body fat monitor embedded in the hollow area; the body fat monitor including a housing and a set of measurement components disposed in the housing, and the set of measurement components at least having an electrical contact exposed from the housing and a top surface of the body fat monitor being flush with a top surface of the base layer;
   wherein the cloth layer has a sensor portion disposed corresponding to the electrical contact, and the electrical contact is directly contacted with the sensor portion, and the sensor portion is configured by conductive yarn knitted on the cloth layer and the conductive yarn is exposed on an upper surface and a lower surface of the cloth layer;
   wherein the top surface of the base layer excluding the hollow area is large enough for a user to stand thereon;
   wherein the top surface of the body fat monitor is exposed at the top surface of the base layer.

2. The carpet type body fat monitor structure according to claim 1, wherein the cloth layer is adhered to the base layer.

3. The carpet type body fat monitor structure according to claim 1, wherein the base layer of the foot pad is made of rubber, sponge or foam material.

4. The carpet type body fat monitor structure according to claim 1, wherein the base layer of the foot pad is made of cloth material and is integrally woven with the cloth layer.

5. The carpet type body fat monitor structure according to claim 1, wherein the cloth layer comprises a barrier cloth and a fold surrounding at a periphery of the barrier cloth.

6. The carpet type body fat monitor structure according to claim 5, wherein the barrier cloth is a blanket or carpet.

7. The carpet type body fat monitor structure according to claim 5, wherein the fold is a partial covering structure which is inwardly recessed from the periphery of the barrier cloth for covering a periphery of the base layer.

8. The carpet type body fat monitor structure according to claim 7, wherein the fold and the barrier cloth are integrally knitted by a same textile material.

9. The carpet type body fat monitor structure according to claim 1, wherein the housing comprises an upper cover and a base, and the electrical contact is exposed from a surface of the upper cover.

10. The carpet type body fat monitor structure according to claim 9, wherein a plurality of foot pads is arranged under the base.

11. The carpet type body fat monitor structure according to claim 1, wherein the set of measurement components further comprises a control printed circuit board (PCB); the electrical contact is electrically connected on the control PCB, and a conductive spring plate is disposed between the electrical contact and the control PCB.

12. The carpet type body fat monitor structure according to claim 1, wherein the electrical contact is composed of conductive metal or conductive silicone.

13. The carpet type body fat monitor structure according to claim 1, wherein the top surface of the base layer excluding the hollow area is larger than the top surface of the body fat monitor.

\* \* \* \* \*